(12) United States Patent
Mederski et al.

(10) Patent No.: US 7,557,222 B2
(45) Date of Patent: Jul. 7, 2009

(54) 1-[(4-ETHYNYLPHENYL)]-2-[(PHENYL)]-PYRROLIDINE-1,2-DICARBOXAMIDE DERIVATIVES AS INHIBITORS OF COAGULATION FACTORS XA AND VIIA FOR THE TREATMENT OF THROMBOSIS

(75) Inventors: Werner Mederski, Zwingenberg (DE); Christos Tsaklakidis, Weinheim (DE); Dieter Dorsch, Ober-Ramstadt (DE); Bertram Cezanne, Mörfelden-Walldorf (DE); Johannes Gleitz, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 88 days.

(21) Appl. No.: 10/561,227

(22) PCT Filed: May 27, 2004

(86) PCT No.: PCT/EP2004/005717

§ 371 (c)(1), (2), (4) Date: Dec. 19, 2005

(87) PCT Pub. No.: WO2004/110433

PCT Pub. Date: Dec. 23, 2004

(65) Prior Publication Data

US 2007/0093472 A1     Apr. 26, 2007

(30) Foreign Application Priority Data

Jun. 18, 2003 (DE) .................. 103 27 428
Jul. 1, 2003 (DE) .................. 103 29 457

(51) Int. Cl.
C07D 227/04 (2006.01)
(52) U.S. Cl. ...................................... 548/538
(58) Field of Classification Search .............. 548/538
See application file for complete search history.

(56) References Cited

U.S. PATENT DOCUMENTS

2003/0162787 A1* 8/2003 Bigge et al. ............ 514/252.03

FOREIGN PATENT DOCUMENTS

WO    WO 02079145 A1    10/2002
WO    WO 03045912 A1    6/2003

OTHER PUBLICATIONS

U.S. Appl. No. 10/594,024, filed Sep. 2006, Mederski, et al.*
Tinnitus [online], retrieved on May 27, 2008, retrieved from the Internet (URL:http://www.nlm.nih.gov/medlineplus/ency/article/003043.htm).*
Migraine [online], retrieved on May 27, 2008, retrieved from the Internet (URL:http://www.thebrainmatter.org/index.cfm?key=1.9.6).*

* cited by examiner

*Primary Examiner*—Rebecca L Anderson
*Assistant Examiner*—Shawquia Young
(74) *Attorney, Agent, or Firm*—Millen, White, Zelano, Branigan, P.C.

(57) ABSTRACT

Novel compounds of the formula (I), in which R, $R^1$, $R^2$ and $R^3$ are as defined in Patent Claim 1, are inhibitors of coagulation factor Xa and can be employed for the prophylaxis and/or therapy of thromboembolic diseases and for the treatment of tumors.

15 Claims, No Drawings

1-[(4-ETHYNYLPHENYL)]-2-[(PHENYL)]-PYRROLIDINE-1,2-DICARBOXAMIDE DERIVATIVES AS INHIBITORS OF COAGULATION FACTORS XA AND VIIA FOR THE TREATMENT OF THROMBOSIS

The invention relates to compounds of the formula I

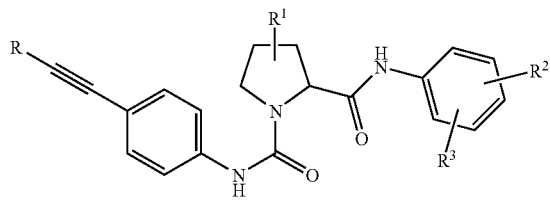

in which
R is H, X, A, X—CO— or A-CO—,
$R^1$ is H, =O, Hal, X, A, OH, OA, A-COO—, A-CONH—, A-CONA-, $N_3$, $NH_2$, $NO_2$, CN, COOH, COOA, $CONH_2$, $CON(A)_2$, O-allyl, O-propargyl, O-benzyl, =N—OH, =N-OA, $OCH_2CH(OH)CH_2OH$, A-O—CO—$(CH_2)_m$—O—, —$O(CH_2)_m COOH$ or —$O(CH_2)_m OA$,
$R^2$ is H, Hal or A,
$R^3$ is a monocyclic saturated, unsaturated or aromatic heterocyclic radical having from 1 to 4 N, O and/or S atoms, which may be unsubstituted or mono-, di- or trisubstituted by Hal, A, OA, CN, $(CH_2)_n OH$, $NR^4R^5$, =NH, =N—OH, =N—OA, COOA and/or carbonyl oxygen (=O), or $CONR^4R^5$,
$R^2$ and $R^3$ together are alternatively —CH=CH—NH— or —$CH_2$—$CH_2$—NH, where one H atom may be replaced by A-CO— or A-O—CO—,
$R^4$ and $R^5$, independently of one another, are H or A,
$R^4$ and $R^5$ together are alternatively an alkylene chain having 3, 4 or 5 carbon atoms, which may also be substituted by A, Hal, OA and/or carbonyl oxygen (=CO),
X is aryl, arylalkyl, Het or Het-alkyl,
aryl is phenyl, naphthyl or biphenyl, each of which is unsubstituted or mono-, di- or trisubstituted by Hal, A, OH, $NH_2$, $NO_2$, CN, COOH, COOA, $CONH_2$, NHCOA, $NHCONH_2$, $NHSO_2A$, CHO, COA, $SO_2NH_2$, $SO_2A$, —$CH_2$—COOH or —$OCH_2$—COOH,
Het is a mono- or bicyclic saturated, unsaturated or aromatic heterocyclic radical having from 1 to 4 N, O and/or S atoms, which may be unsubstituted or mono-, di- or trisubstituted by Hal, A, benzyl, cycloalkyl, OH, $NH_2$, $NHCONH_2$, $NO_2$, CN, —$CH_2$—COOH, —$CH_2$—$CONH_2$, NHCOA, $NR^3SO_2A$, CHO, $SO_2NH_2$, $SO_2A$ and/or carbonyl oxygen,
A is unbranched, branched or cyclic alkyl having 1-10 carbon atoms, in which, in addition, 1-7 H atoms may be replaced by F and/or chlorine,
Hal is F, Cl, Br or I,
m is 1, 2, 3, 4, 5 or 6,
n is 0, 1, 2, 3, 4, 5 or 6,
and pharmaceutically usable derivatives, salts, solvates and stereoisomers thereof, including mixtures thereof in all ratios.

The invention also relates to the optically active forms, the racemates, the diastereomers and the hydrates and solvates, for example alcoholates, of these compounds.

The invention had the object of finding novel compounds having valuable properties, in particular those which can be used for the preparation of medicaments.

It has been found that the compounds of the formula I and salts thereof have very valuable pharmacological properties and are well tolerated. In particular, they exhibit factor Xa-inhibiting properties and can therefore be employed for combating and preventing thromboembolic diseases, such as thrombosis, myocardial infarction, arteriosclerosis, inflammation, apoplexia, angina pectoris, restenosis after angioplasty and claudicatio intermittens.

The compounds of the formula I according to the invention are furthermore inhibitors of the coagulation factors factor VIIa, factor IXa and thrombin in the blood coagulation cascade.

Other ethynyl derivatives are described as factor Xa inhibitors in WO 02/079145.

Other aromatic amides are described in WO 99/00121 and in WO 00/39118.

Aromatic amidine derivatives having an antithrombotic action are disclosed, for example, in EP 0 540 051 B1. Cyclic guanidines for the treatment of thromboembolic diseases are described, for example, in WO 97/08165. Aromatic heterocyclic compounds having a factor Xa inhibitory activity are disclosed, for example, in WO 96/10022. Substituted N-[(aminoiminomethyl)phenylalkyl]azaheterocyclylamides as factor Xa inhibitors are described in WO 96/40679.

The antithrombotic and anticoagulant effect of the compounds according to the invention is attributed to the inhibitory action against activated coagulation protease, known by the name factor Xa, or to the inhibition of other activated serine proteases, such as factor VIIa, factor IXa or thrombin.

Factor Xa is one of the proteases involved in the complex process of blood coagulation. Factor Xa catalyses the conversion of prothrombin into thrombin. Thrombin cleaves fibrinogen into fibrin monomers, which, after crosslinking, make an elementary contribution to thrombus formation. Activation of thrombin may result in the occurrence of thromboembolic diseases. However, inhibition of thrombin may inhibit the fibrin formation involved in thrombus formation.

The inhibition of thrombin can be measured, for example by the method of G. F. Cousins et al. in *Circulation* 1996, 94, 1705-1712.

Inhibition of factor Xa can thus prevent the formation of thrombin.

The compounds of the formula I according to the invention and salts thereof engage in the blood coagulation process by inhibiting factor Xa and thus inhibit the formation of thrombuses.

The inhibition of factor Xa by the compounds according to the invention and the measurement of the anticoagulant and antithrombotic activity can be determined by conventional in-vitro or in-vivo methods. A suitable method is described, for example, by J. Hauptmann et al. in *Thrombosis and Haemostasis* 1990, 63, 220-223.

The inhibition of factor Xa can be measured, for example by the method of T. Hara et al. in *Thromb. Haemostas.* 1994, 71, 314-319.

Coagulation factor VIIa initiates the extrinsic part of the coagulation cascade after binding to tissue factor and contributes to the activation of factor X to give factor Xa. Inhibition of factor VIIa thus prevents the formation of factor Xa and thus subsequent thrombin formation.

The inhibition of factor VIIa by the compounds according to the invention and the measurement of the anticoagulant and antithrombotic activity can be determined by conventional in-vitro or in-vivo methods. A conventional method for the measurement of the inhibition of factor VIIa is described, for example, by H. F. Ronning et al. in *Thrombosis Research* 1996, 84, 73-81.

Coagulation factor IXa is generated in the intrinsic coagulation cascade and is likewise involved in the activation of factor X to give factor Xa. Inhibition of factor IXa can therefore prevent the formation of factor Xa in a different way.

The inhibition of factor IXa by the compounds according to the invention and the measurement of the anticoagulant and antithrombotic activity can be determined by conventional in-vitro or in-vivo methods. A suitable method is described, for example, by J. Chang et al. in *Journal of Biological Chemistry* 1998, 273, 12089-12094.

The compounds according to the invention may furthermore be used for the treatment of tumours, tumour diseases and/or tumour metastases.

A correlation between tissue factor TF/factor VIIa and the development of various types of cancer has been indicated by T. Taniguchi and N. R. Lemoine in Biomed. Health Res. (2000), 41 (Molecular Pathogenesis of Pancreatic Cancer), 57-59.

The publications listed below describe an antitumoral action of TF-VII and factor Xa inhibitors in various types of tumour:
K. M. Donnelly et al. in Thromb. Haemost. 1998; 79: 1041-1047;
E. G. Fischer et al. in J. Clin. Invest. 104: 1213-1221 (1999);
B. M. Mueller et al. in J. Clin. Invest. 101: 1372-1378 (1998);
M. E. Bromberg et al. in Thromb. Haemost. 1999; 82: 88-92

The compounds of the formula I can be employed as medicament active ingredients in human and veterinary medicine, in particular for the treatment and prevention of thromboembolic diseases, such as thrombosis, myocardial infarction, arteriosclerosis, inflammation, apoplexia, angina pectoris, restenosis after angioplasty, claudicatio intermittens, venous thrombosis, pulmonary embolism, arterial thrombosis, myocardial ischaemia, unstable angina and strokes based on thrombosis.

The compounds according to the invention are also employed for the treatment or prophylaxis of atherosclerotic diseases, such as coronary arterial disease, cerebral arterial disease or peripheral arterial disease.

The compounds are also employed in combination with other thrombolytic agents in myocardial infarction, furthermore for prophylaxis for reocclusion after thrombolysis, percutaneous transluminal angioplasty (PTCA) and coronary bypass operations.

The compounds according to the invention are furthermore used for the prevention of rethrombosis in microsurgery, furthermore as anticoagulants in connection with artificial organs or in haemodialysis.

The compounds are furthermore used in the cleaning of catheters and medical aids in patients in vivo, or as anticoagulants for the preservation of blood, plasma and other blood products in vitro. The compounds according to the invention are furthermore used for diseases in which blood coagulation makes a crucial contribution toward the course of the disease or represents a source of secondary pathology, such as, for example, in cancer, including metastasis, inflammatory diseases, including arthritis, and diabetes.

The compounds according to the invention are furthermore used for the treatment of migraine (F. Morales-Asin et al., Headache, 40, 2000, 45-47). In addition, they can be used for the treatment of tinnitus. The use of anticoagulants in tinnitus therapy is described by R. Mora et al. in International Tinnitus Journal (2003), 9(2), 109-111.

In the treatment of the diseases described, the compounds according to the invention are also employed in combination with other thrombolytically active compounds, such as, for example, with the "tissue plasminogen activator" t-PA, modified t-PA, streptokinase or urokinase. The compounds according to the invention are administered either at the same time as or before or after the other substances mentioned.

Particular preference is given to simultaneous administration with aspirin in order to prevent recurrence of the clot formation.

The compounds according to the invention are also used in combination with blood platelet glycoprotein receptor (IIb/IIIa) antagonists, which inhibit blood platelet aggregation.

The invention relates to the compounds of the formula I and salts thereof and to a process for the preparation of compounds of the formula I according to claim 1 and salts thereof, characterised in that a) a compound of the formula II

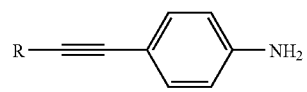

in which R is as defined in claim 1, is reacted with a chloroformate derivative to give a carbamate derivative intermediate, which is subsequently reacted with a compound of the formula III

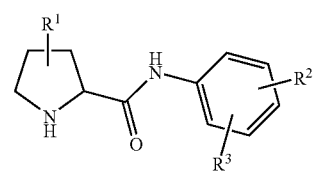

in which
$R^1$, $R^2$ and $R^3$ are as defined in claim 1,
or b) a compound of the formula III
is reacted with a compound of the formula IV

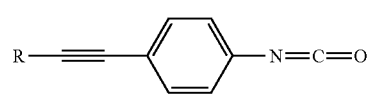

in which
R is as defined in claim 1,
or
c) a compound of the formula V

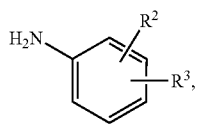

in which $R^2$ and R are as defined in claim 1,
is reacted with a compound of the formula VI

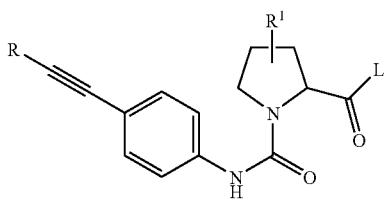

in which
L is Cl, Br, I or a free or reactively functionally modified OH group, and
R and $R^1$ are as defined in claim 1,
and/or a base or acid of the formula I is converted into one of its salts.

The invention also relates to the optically active forms (stereoisomers), the enantiomers, the racemates, the diastereomers and the hydrates and solvates of these compounds. The term "solvates of the compounds" is taken to mean adductions of inert solvent molecules onto the compounds which form owing to their mutual attractive force. Solvates are, for example, mono- or dihydrates or alcoholates.

The term "pharmaceutically usable derivatives" is taken to mean, for example, the salts of the compounds according to the invention and so-called prodrug compounds.

The term "prodrug derivatives" is taken to mean compounds of the formula I which have been modified with, for example, alkyl or acyl groups, sugars or oligopeptides and which are rapidly cleaved in the organism to form the active compounds according to the invention.

These also include biodegradable polymer derivatives of the compounds according to the invention, as described, for example, in Int. J. Pharm. 115, 61-67 (1995).

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

For all radicals which occur more than once, their meanings are independent of one another.

Above and below, the radicals or parameters R, $R^1$, $R^2$ and $R^3$ are as defined under the formula I, unless expressly stated otherwise.

A is alkyl, is unbranched (linear) or branched and has 1, 2, 3, 4, 5, 6, 7, 8, 9 or 10 carbon atoms. A is preferably methyl, furthermore ethyl, propyl, isopropyl, butyl, isobutyl, sec-butyl or tert-butyl, furthermore also pentyl, 1-, 2- or 3-methylbutyl, 1,1'-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A is very particularly preferably alkyl having 1, 2, 3, 4, 5 or 6 carbon atoms, preferably methyl, ethyl, propyl, isopropyl, butyl, isobutyl, sec-butyl, tert-butyl, pentyl, hexyl or trifluoromethyl.

A is alternatively cycloalkyl. Cycloalkyl preferably has 3-7 carbon atoms.

Hal is preferably F, Cl or Br, but alternatively 1.

$R^1$ is preferably H, =O, Hal, aryl, Het, A, OH, OA, A-COO—, A-CONH—, A-CONA-, $N_3$, $NH_2$, $NO_2$, CN, COOH, COOA, $CONH_2$, $CON(A)_2$, O-allyl, O-propargyl, O-benzyl, =N—OH, =N-OA, $OCH_2CH(OH)CH_2OH$, A-O—CO—$(CH_2)_m$—O—, —$O(CH_2)_m$COOH or —$O(CH_2)_m$OA, particularly preferably H, OH, O-allyl, O-propargyl, $OCH_2CH(OH)CH_2OH$, A-O—CO—$(CH_2)_m$—O—, such as, for example, methoxycarbonylmethoxy; —$O(CH_2)_m$COOH, such as, for example, carboxymethoxy; OA, such as, for example, methoxy or ethoxy; or $O(CH_2)_m$OA, such as, for example, methoxyethoxy.

$R^3$ is preferably a monocyclic saturated, unsaturated or aromatic heterocyclic radical having from 1 to 4 N, O and/or S atoms, which may be unsubstituted or mono-, di- or trisubstituted by Hal, A, OA, =NH, OH, COOA and/or carbonyl oxygen (=O),
or $R^3$ is $CONR^4R^5$.

In particular, $R^3$ is 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2-iminopiperidin-1-yl, 2-iminopyrrolidin-1-yl, 3-iminomorpholin-4-yl, 2-iminoimidazolidin-1-yl, 2-imino-1H-pyrazin-1-yl, 2,6-dioxopiperidin-1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl(=2-oxoazepan-1-yl), 2-azabicyclo[2.2.2]octan-3-on-2-yl, 5,6-dihydro-1H-pyrimidin-2-oxo-1-yl, 2-oxo-1,3-oxazinan-3-yl, 4H-1,4-oxazin-4-yl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl or pyrazinyl,
optionally mono- or disubstituted by Hal, OH, COOA, OA and/or A,
or
$CONR^4R^5$.

$R^3$ is particularly preferably 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2-oxopiperazin-1-yl, 3-oxo-2H-pyridazin-2-yl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl or pyrazinyl,
optionally mono- or disubstituted by Hal, OH, COOA, OA and/or A,
or $CONR^4R^5$, where
$R^4$ and $R^5$ together are an alkylene chain having 3, 4 or 5 carbon atoms.

$R^2$ and $R^3$ together are alternatively —CH=CH—NH— or —$CH_2$—$CH_2$—NH, where one H atom may be replaced by A-CO— or A-O—CO—, such as, for example, by acetyl or ethoxycarbonyl.

Aryl is preferably phenyl, naphthyl or biphenyl, each of which is unsubstituted or mono-, di- or trisubstituted by Hal, A, OH, $NH_2$, $NO_2$, CN, COOH, COOA, $CONH_2$, NHCOA, NHCONH$_2$, NHSO$_2$A, CHO, COA, SO$_2$NH$_2$, SO$_2$A, —CH$_2$—COOH or —OCH$_2$—COOH.

Aryl is, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

"Alkyl" in arylalkyl or Het-alkyl is, for example, methylene, ethylene or propylene.

Het is, for example, 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, furthermore preferably 1,3-benzodioxol-5-yl, 1,4-benzodioxan-6-yl, 2,1,3-benzothiadiazol-4- or -5-yl or 2,1,3-benzoxadiazol-5-yl.

The heterocyclic radicals may also be partially or fully hydrogenated. Het can thus also be, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, 4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or alternatively 3,4-dihydro-2H-1,5-benzodioxepin-6- or -7-yl, furthermore preferably 2,3-dihydrobenzofuranyl or 2,3-dihydro-2-oxofuranyl.

The compounds of the formula I can have one or more centres of chirality and can therefore occur in various stereoisomeric forms. The formula I covers all these forms.

Accordingly, the invention relates, in particular, to compounds of the formula I in which at least one of the said radicals has one of the preferred meanings indicated above. Some preferred groups of compounds can be expressed by the following sub-formulae Ia to Ij, which conform to the formula I and in which the radicals not designated in greater detail are as defined under the formula I, but in which in Ia R is H or A;

in Ib R$^3$ is a monocyclic saturated, unsaturated or aromatic heterocyclic radical having from 1 to 4 N, O and/or S atoms, which may be unsubstituted or mono-, di- or trisubstituted by Hal, A, OA, =NH, OH, COOA and/or carbonyl oxygen (=O), or CONR$^4$R$^5$;

in Ic R$^3$ is 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2-iminopiperidin-1-yl, 2-iminopyrrolidin-1-yl, 3-iminomorpholin-4-yl, 2-iminoimidazolidin-1-yl, 2-imino-1H-pyrazin-1-yl, 2,6-dioxopiperidin-1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl (=2-oxoazepan-1-yl), 2-azabicyclo[2.2.2]octan-3-on-2-yl, 5,6-dihydro-1H-pyrimidin-2-oxo-1-yl, 2-oxo-1,3-oxazinan-3-yl, 4H-1,4-oxazin-4-yl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl or pyrazinyl, optionally mono- or disubstituted by Hal, OA, OH, COOA and/or A, or

CONR$^4$R$^5$,

R$^4$ and R$^5$, independently of one another, are H or A,

R$^4$ and R$^5$ together are alternatively an alkylene chain having 3, 4 or 5 carbon atoms;

in Id R is H, X, A, X—CO— or A-CO—,

R$^1$ is H, =O, Hal, X, A, OH, OA, A-COO—, A-CONH—, A-CONA-, N$_3$, NH$_2$, NO$_2$, CN, COOH, COOA, CONH$_2$, CON(A)$_2$, O-allyl, O-propargyl, O-benzyl, =N—OH, =N-OA, OCH$_2$CH(OH)CH$_2$OH, A-O—CO—(CH$_2$)$_m$—O—, O(CH$_2$)$_m$COOH or —O(CH$_2$)$_m$OA, R$^2$ is H, Hal or A, R$^3$ is 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2-iminopiperidin-1-yl, 2-iminopyrrolidin-1-yl, 3-iminomorpholin-4-yl, 2-iminoimidazolidin-1-yl, 2-imino-1H-pyrazin-1-yl, 2,6-dioxopiperidin-1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl (=2-oxoazepan- 1-yl), 2-azabicyclo[2.2.2]octan-3-on-2-yl, 5,6-dihydro-1H-pyrimidin-2-oxo-1-yl, 2-oxo-1,3-oxazinan-3-yl, 4H-1,4-oxazin-4-yl,
furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl or pyrazinyl,
optionally mono- or disubstituted by Hal, OA, OH, COOA and/or A,
or
$CONR^4R^5$,
$R^4$ and $R^5$, independently of one another, are H or A,
$R^4$ and $R^5$ together are alternatively an alkylene chain having 3, 4 or 5 carbon atoms,
X is aryl, arylalkyl, Het or Het-alkyl,
aryl is phenyl, naphthyl or biphenyl, each of which is unsubstituted or mono-, di- or trisubstituted by Hal, A, OH, $NH_2$, $NO_2$, CN, COOH, COOA, $CONH_2$, NHCOA, $NHCONH_2$, $NHSO_2A$, CHO, COA, $SO_2NH_2$, $SO_2A$, $—CH_2—COOH$ or $—OCH_2—COOH$,
Het is a mono- or bicyclic saturated, unsaturated or aromatic heterocyclic radical having from 1 to 4 N, O and/or S atoms, which may be unsubstituted or mono-, di- or trisubstituted by Hal, A, benzyl, cycloalkyl, OH, $NH_2$, $NHCONH_2$, $NO_2$, CN, $—CH_2—COOH$, $—CH_2—CONH_2$, NHCOA, $NR^3SO_2A$, CHO, $SO_2NH_2$, $SO_2A$ and/or carbonyl oxygen,
A is unbranched, branched or cyclic alkyl having 1-10 carbon atoms, in which, in addition, 1-7 H atoms may be replaced by F,
Hal is F, Cl, Br or I;
in Ie R is H or A,
$R^1$ is H, OH, OA, O-allyl, O-propargyl, $OCH_2CH(OH)CH_2OH$, $A-O—CO—(CH_2)_m—O—$, $—O(CH_2)_m COOH$ or $—O(CH_2)_m OA$,
$R^2$ is H, Hal or A,
$R^3$ is 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2-oxopiperazin-1-yl, 3-oxo-2H-pyridazin-2-yl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl or pyrazinyl, optionally mono- or disubstituted by Hal, OA, OH, COOA and/or A,
or $CONR^4R^5$,
$R^4$ and $R^5$ together are an alkylene chain having 3, 4 or 5 carbon atoms,
A is unbranched, branched or cyclic alkyl having 1-10 carbon atoms, in which, in addition, 1-7 H atoms may be replaced by F,
Hal is F, Cl, Br or I;
in If R is H, X, A, X—CO— or A-CO—,
$R^1$ is H, =O, Hal, X, A, OH, OA, A-COO—, A-CONH—, A-CONA-, $N_3$, $NH_2$, $NO_2$, CN, COOH, COOA, $CONH_2$, $CON(A)_2$, O-allyl, O-propargyl, O-benzyl, =N—OH, =N—OA, $OCH_2CH(OH)CH_2OH$, $A-O—CO—(CH_2)_m—O—$, $—O(CH_2)_m COOH$ or $—O(CH_2)_m OA$,
$R^2$ is H, Hal or A,
$R^3$ is 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2-iminopiperidin-1-yl, 2-iminopyrrolidin-1-yl, 3-iminomorpholin-4-yl, 2-iminoimidazolidin-1-yl, 2-imino-1H-pyrazin-1-yl, 2,6-dioxopiperidin-1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl (=2-oxoazepan-1-yl), 2-azabicyclo[2.2.2]octan-3-on-2-yl, 5,6-dihydro-1H-pyrimidin-2-oxo-1-yl, 2-oxo-1,3-oxazinan-3-yl or 4H-1,4-oxazin-4-yl,
X is aryl, arylalkyl, Het or Het-alkyl,
aryl is phenyl, naphthyl or biphenyl, each of which is unsubstituted or mono-, di- or trisubstituted by Hal, A, OH, $NH_2$, $NO_2$, CN, COOH, COOA, $CONH_2$, NHCOA, $NHCONH_2$, $NHSO_2A$, CHO, COA, $SO_2NH_2$, $SO_2A$, $—CH_2—COOH$ or $—OCH_2—COOH$,
Het is a mono- or bicyclic saturated, unsaturated or aromatic heterocyclic radical having from 1 to 4 N, O and/or S atoms, which may be unsubstituted or mono-, di- or trisubstituted by Hal, A, benzyl, cycloalkyl, OH, $NH_2$, $NHCONH_2$, $NO_2$, CN, $—CH_2—COOH$, $—CH_2—CONH_2$, NHCOA, $NR^3SO_2A$, CHO, $SO_2NH_2$, $SO_2A$ and/or carbonyl oxygen,
A is unbranched, branched or cyclic alkyl having 1-10 carbon atoms, in which, in addition, 1-7 H atoms may be replaced by F,
Hal is F, Cl, Br or I;
in Ig $R^3$ is 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2-oxopiperazin-1-yl or 3-oxo-2H-pyridazin-2-yl;
in Ih $R^1$ is H, OH, OA, O-allyl, O-propargyl, $OCH_2CH(OH)CH_2OH$, $A-O—CO—(CH_2)_m—O—$, $—O(CH_2)_m COOH$ or $—O(CH_2)_m OA$;
in Ii A is unbranched or branched alkyl having 1-6 carbon atoms;
in Ij R is H or A,
$R^1$ is H, OH, OA, O-allyl, O-propargyl, $OCH_2CH(OH)CH_2OH$, $A-O—CO—(CH_2)_m—O—$, $—O(CH_2)_m COOH$ or $—O(CH_2)_m OA$,
$R^2$ is H, Hal or A,
$R^3$ is 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2-oxopiperazin-1-yl or 3-oxo-2H-pyridazin-2-yl, optionally monosubstituted by A, OH or COOA,
A is unbranched, branched or cyclic alkyl having 1-10 carbon atoms, in which, in addition, 1-7 H atoms may be replaced by F,
Hal is F, Cl, Br or I, and pharmaceutically usable derivatives, salts, solvates and stereoisomers thereof, including mixtures thereof in all ratios.

The compounds of the formula I and also the starting materials for the preparation thereof are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail.

If desired, the starting materials can also be formed in situ so that they are not isolated from the reaction mixture, but instead are immediately converted further into the compounds of the formula I.

Compounds of the formula I can preferably be obtained by reacting compounds of the formula II with a chloroformate derivative, for example 4-nitrophenyl chloroformate, to give a carbamate intermediate and subsequently reacting with compounds of the formula III.

The reaction is generally carried out in an inert solvent, in the presence of an acid-binding agent, preferably an alkali or alkaline earth metal hydroxide, carbonate or bicarbonate or another salt of a weak acid of the alkali or alkaline earth metals, preferably of potassium, sodium, calcium or caesium. It may also be favourable to add an organic base, such as triethylamine, dimethylaniline, pyridine or quinoline. Depending on the conditions used, the reaction time is between a few minutes and 14 days, and the reaction temperature is between about 0° and 150°, normally between 20° and 130°.

Examples of suitable inert solvents are water; hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

The starting compounds of the formulae II and III are generally known. If they are novel, however, they can be prepared by methods known per se.

Compounds of the formula I can also be obtained by reacting compounds of the formula III with compounds of the formula IV.

This is carried out under conditions as described above.

The starting compounds of the formula IV are generally known. If they are novel, however, they can be prepared by methods known per se.

Compounds of the formula I can also be obtained by reacting compounds of the formula V with compounds of the formula VI.

In the compounds of the formula VI, L is preferably Cl, Br, I or a reactively modified OH group, such as, for example, an activated ester, an imidazolide or alkylsulfonyloxy having 1-6 carbon atoms (preferably methylsulfonyloxy or trifluoromethylsulfonyloxy) or arylsulfonyloxy having 6-10 carbon atoms (preferably phenyl- or p-tolylsulfonyloxy).

Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart).

Activated esters are advantageously formed in situ, for example through addition of HOBt or N-hydroxysuccinimide.

The reaction is generally carried out in an inert solvent, in the presence of an acid-binding agent, preferably an alkali or alkaline earth metal hydroxide, carbonate or bicarbonate or another salt of a weak acid of the alkali or alkaline earth metals, preferably of potassium, sodium, calcium or caesium. It may also be favourable to add an organic base, such as triethylamine, dimethylaniline, pyridine or quinoline, or an excess of the amine component of the formula IV. Depending on the conditions used, the reaction time is between a few minutes and 14 days, and the reaction temperature is between about 0° and 150°, normally between 20° and 130°.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

The compounds of the formula VI are generally novel and are obtained by reaction of the compounds of the formula IV with compounds of the formula VII

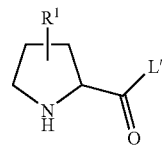

VII

In the compounds of the formula VII, L' is, for example, OH and $R^1$ is as defined in claim 1.

Esters can be saponified, for example, using acetic acid or using NaOH or KOH in water, water/THF or water/dioxane at temperatures between 0 and 100°.

A base of the formula I can be converted into the associated acid-addition salt using an acid, for example by reaction of equivalent amounts of the base and the acid in an inert solvent, such as ethanol, followed by evaporation. Suitable acids for this reaction are, in particular, those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, or sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, and laurylsulfuric acid. Salts with physiologically unacceptable acids, for example picrates, can be used for the isolation and/or purification of the compounds of the formula I.

On the other hand, compounds of the formula I can be converted into the corresponding metal salts, in particular alkali metal or alkaline earth metal salts, or into the corresponding ammonium salts using bases (for example sodium hydroxide, potassium hydroxide, sodium carbonate or potassium carbonate).

It is also possible to use physiologically acceptable organic bases, such as, for example, ethanolamine.

Compounds of the formula I according to the invention may be chiral owing to their molecular structure and may accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of the compounds of the formula I and/or physiologically acceptable salts thereof for the preparation of pharmaceutical preparations, in particular by non-chemical methods. They can be converted here into a suitable dosage form together with at least one solid, liquid and/or semi-liquid excipient or adjuvant and, if desired, in combination with one or more further active ingredients.

The invention furthermore relates to medicaments comprising at least one compound of the formula I and/or pharmaceutically usable derivatives, solvates and stereoisomers thereof, including mixtures thereof in all ratios, and, if desired, excipients and/or adjuvants.

These medicaments can be used in human or veterinary medicine. Suitable excipients are organic or inorganic substances which are suitable for enteral (for example oral), parenteral or topical administration and do not react with the novel compounds, for example water, vegetable oils, benzyl alcohols, alkylene glycols, polyethylene glycols, glycerol triacetate, gelatine, carbohydrates, such as lactose or starch, magnesium stearate, talc or Vaseline. Suitable for oral administration are, in particular, tablets, pills, coated tablets, capsules, powders, granules, syrups, juices or drops, suitable for rectal administration are suppositories, suitable for parenteral administration are solutions, preferably oil-based or aqueous solutions, furthermore suspensions, emulsions or implants, and suitable for topical application are ointments, creams or powders or also as nasal sprays. The novel compounds may also be lyophilised and the resultant lyophilisates used, for example, to prepare injection preparations. The preparations indicated may be sterilised and/or comprise adjuvants, such as lubricants, preservatives, stabilisers and/or wetting agents, emulsifying agents, salts for modifying the osmotic pressure, buffer substances, colorants and flavours and/or a plurality of further active ingredients, for example one or more vitamins.

The compounds of the formula I and physiologically acceptable salts thereof can be used for combating and preventing thromboembolic diseases, such as thrombosis, myocardial infarction, arteriosclerosis, inflammation, apoplexia, angina pectoris, restenosis after angioplasty, claudicatio intermittens, migraine, tumours, tumour diseases and/or tumour metastases.

In general, the substances according to the invention are preferably administered in doses between about 1 and 500 mg, in particular between 5 and 100 mg, per dosage unit. The daily dose is preferably between about 0.02 and 10 mg/kg of body weight. However, the specific dose for each patient depends on a wide variety of factors, for example on the efficacy of the specific compound employed, on the age, body weight, general state of health, sex, on the diet, on the time and method of administration, on the excretion rate, medicament combination and severity of the particular disease to which the therapy applies. Oral administration is preferred.

The invention furthermore relates to medicaments comprising at least one compound of the formula I and/or pharmaceutically usable derivatives, salts, solvates and stereoisomers thereof, including mixtures thereof in all ratios, and at least one further medicament active ingredient.

The invention also relates to a set (kit) consisting of separate packs of (a) an effective amount of a compound of the formula I and/or pharmaceutically usable derivatives, solvates and stereoisomers thereof, including mixtures thereof in all ratios, and (b) an effective amount of a further medicament active ingredient.

The set comprises suitable containers, such as boxes, individual bottles, bags or ampoules. The set may, for example, comprise separate ampoules each containing an effective amount of a compound of the formula I and/or pharmaceutically usable derivatives, salts, solvates and stereoisomers thereof, including mixtures thereof in all ratios, and an effective amount of a further medicament active ingredient in dissolved or lyophilised form.

The invention furthermore relates to the use of compounds of the formula I and/or pharmaceutically usable derivatives, salts, solvates and stereoisomers thereof, including mixtures thereof in all ratios, for the preparation of a medicament for the treatment of thromboses, myocardial infarction, arteriosclerosis, inflammation, apoplexia, angina pectoris, restenosis after angioplasty, claudicatio intermittens, migraine, tinnitus, tumours, tumour diseases and/or tumour metastases, in combination with at least one further medicament active ingredient.

Above and below, all temperatures are given in ° C. In the following examples, "conventional work-up" means that water is added if necessary, the pH is adjusted, if necessary, to between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. Rf values on silica gel; eluent:ethyl acetate/methanol 9:1.

Mass spectrometry (MS): EI (electron impact ionisation) M$^+$ESI (electrospray ionisation) (M+H)$^+$FAB (fast atom bombardment) (M+H)$^+$

EXAMPLE 1

1-[(4-ethynylphenyl)]-2-{[4-(2-oxo-2H-pyridin-1-yl)phenyl]}-(2R,4R)-4-methoxypyrrolidine-1,2-dicarboxamide ("A1") is prepared analogously to the following scheme:

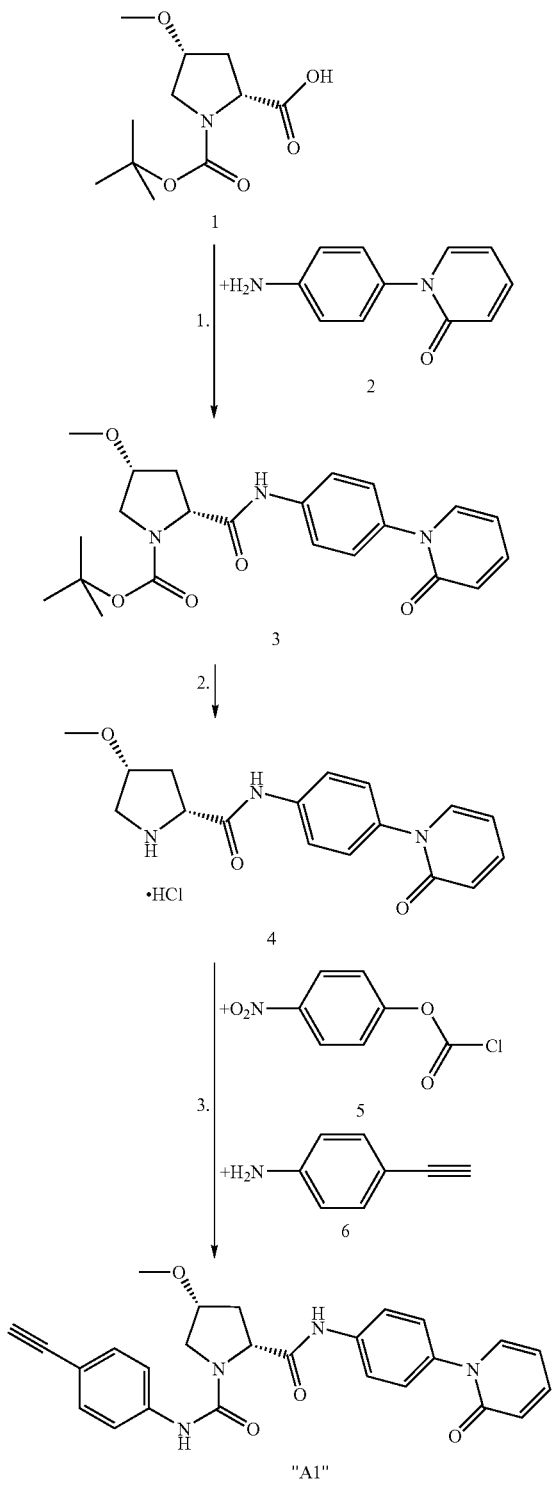

1. 0.76 g (4.076 mmol) of anilinopyridone 2 and 1.008 g (4.076 mmol) of ethyl 2-ethoxy-1,2-dihydroquinoline-1-carboxylate are added successively with stirring at room temperature to 1.0 g (4.076 mmol) of BOC-methoxyproline 1 as a suspension in 15 ml of toluene. The mixture is subsequently stirred at this temperature for 18 hours and then subjected to conventional work-up, giving 1.53 g (90.8%) of BOC-proline anilide derivative 3 as crude product; MS-EI (M+) 414.

2. 1.5 g (3.628 mmol) of 3 are dissolved in 20 ml of dioxane, and 20 ml of 4N HCl in dioxane are added at room temperature, and the mixture is stirred at this temperature for 2 hours and then subjected to conventional work-up, giving 0.94 g (74.1%) of the proline anilide hydrochloride derivative 4 as crude product.

3. 202 mg (1.001 mmol) of 4-nitrophenyl chloroformate 5, 118 mg (1.001 mmol) of 4-ethynylaniline and 0.081 ml (1.001 mmol) of pyridine in 10 ml of dichloromethane are stirred for 1 hour at room temperature under a nitrogen atmosphere. 350 mg (1.001 mmol) of 4 and 0.511 ml (3.003 mmol) of N-ethyldiisopropylamine in 5 ml of dichloromethane are subsequently added. The resultant suspension is stirred at room temperature for a further 2 hours, then subjected to conventional work-up, giving 185 mg (40.5%) of "A1"; MS-EI (M+) 457.

The following compounds are obtained analogously:

1-[(4-ethynylphenyl)]-2-{[4-(3-oxomorpholin-4-yl)-phenyl]}-(2R,4R)-4-methoxypyrrolidine-1,2-dicarboxamide ("A2"), 1-[(4-ethynylphenyl)]-2-{[3-methyl-4-(3-oxomorpholin-4-yl)phenyl]}-(2R,4R)-4-methoxypyrrolidine-1,2-dicarboxamide ("A3"), 1-[(4-ethynylphenyl)]-2-{[4-(3-oxomorpholin-4-yl)-phenyl]}-(2R,4R)-4-hydroxypyrrolidine-1,2-dicarboxamide, 1-[(4-ethynylphenyl)]-2-{[3-methyl-4-(3-oxomorpholin-4-yl)phenyl]}-(2R,4R)-4-ethoxypyrrolidine-1,2-dicarboxamide, 1-[(4-ethynylphenyl)]-2-{[4-(2-oxo-2H-pyridin-1-yl)phenyl]}-(2R,4R)-4-hydroxypyrrolidine-1,2-dicarboxamide, 1-[(4-ethynylphenyl)]-2-{[3-methyl-4-(3-oxomorpholin-4-yl)phenyl]}-(2R,4R)-4-hydroxypyrrolidine-1,2-dicarboxamide, 1-[(4-ethynylphenyl)]-2-{[4-(3-oxomorpholin-4-yl)-phenyl]}-(2R)-pyrrolidine-1,2-dicarboxamide, 1-[(4-ethynylphenyl)]-2-{[3-methyl-4-(3-oxomorpholin-4-yl)phenyl]}-(2R)-pyrrolidine-1,2-dicarboxamide, 1-[(4-ethynylphenyl)]-2-{[4-(2-oxo-2H-pyridin-1-yl)phenyl]}-(2R)-pyrrolidine-1,2-dicarboxamide, 1-[(4-ethynylphenyl)]-2-{[2-fluoro-4-(3-oxomorpholin-4-yl)phenyl]}-(2R,4R)-4-methoxypyrrolidine-1,2-dicarboxamide, m.p. 191-192°;

1-[(4-ethynylphenyl)]-2-{[4-(2-oxo-2H-pyridin-1-yl)phenyl]}-(2R,4R)-4-ethoxypyrrolidine-1,2-dicarboxamide, 1-[(4-ethynylphenyl)]-2-{[3-methyl-4-(3-oxomorpholin-4-yl)phenyl]}-(2R,4R)-4-ethoxypyrrolidine-1,2-dicarboxamide, 1-[(4-ethynylphenyl)]-2-{[2-fluoro-4-(3-oxomorpholin-4-yl)phenyl]}-(2R)-pyrrolidine-1,2-dicarboxamide, 1-[(4-ethynylphenyl)]-2-{[2-fluoro-4-(3-oxomorpholin-4-yl)phenyl]}-(2R,4R)-4-ethoxypyrrolidine-1,2-dicarboxamide, 1-[(4-ethynylphenyl)]-2-{[2-fluoro-4-(3-oxomorpholin-4-yl)phenyl]}-(2R,4R)-4-hydroxypyrrolidine-1,2-dicarboxamide, 1-[(4-ethynylphenyl)]-2-{[4-(2-oxo-1H-pyrazin-1-yl)phenyl]}-(2R,4R)-4-ethoxypyrrolidine-1,2-dicarboxamide.

EXAMPLE 2

The following compounds are obtained analogously to Example 1:
1-[(4-ethynylphenyl)]-2-{[4-(pyrrolidine-1-carbonyl)phenyl]}-(2R,4R)-4-hydroxypyrrolidine-1,2-dicarboxamide,
1-[(4-ethynylphenyl)]-2-{[4-(pyrrolidine-1-carbonyl)phenyl]}-(2R)-4-pyrrolidine-1,2-dicarboxamide,
1-[(4-ethynylphenyl)]-2-{[4-(pyrrolidine-1-carbonyl)phenyl]}-(2R,4R)-4-methoxypyrrolidine-1,2-dicarboxamide,
1-[(4-ethynylphenyl)]-2-{[4-(pyrrolidine-1-carbonyl)phenyl]}-(2R,4R)-4-ethoxypyrrolidine-1,2-dicarboxamide,
1-[(4-ethynylphenyl)]-2-{[2-fluoro-4-(pyrrolidine-1-carbonyl)phenyl]}-(2R,4R)-4-hydroxypyrrolidine-1,2-dicarboxamide,
1-[(4-ethynylphenyl)]-2-{[2-fluoro-4-(pyrrolidine-1-carbonyl)phenyl]}-(2R)-pyrrolidine-1,2-dicarboxamide,
1-[(4-ethynylphenyl)]-2-{[2-fluoro-4-(pyrrolidine-1-carbonyl)phenyl]}-(2R,4R)-4-methoxypyrrolidine-1,2-dicarboxamide,
1-[(4-ethynylphenyl)]-2-{[2-fluoro-4-(pyrrolidine-1-carbonyl)phenyl]}-(2R,4R)-4-ethoxypyrrolidine-1,2-dicarboxamide.

EXAMPLE 3

The following compounds are obtained analogously to Example 1:
1-[(4-ethynylphenyl)]-2-{[2-fluoro-4-(5-methylpyrazol-1-yl)phenyl]}-(2R,4R)-4-hydroxypyrrolidine-1,2-dicarboxamide,
1-[(4-ethynyl phenyl)]-2-{[2-fluoro-4-(5-methylpyrazol-1-yl)phenyl]}-(2R)-pyrrolidine-1,2-dicarboxamide,
1-[(4-ethynylphenyl)]-2-{[2-fluoro-4-(5-methylpyrazol-1-yl)phenyl]}-(2R,4R)-4-methoxypyrrolidine-1,2-dicarboxamide,
1-[(4-ethynylphenyl)]-2-{[2-fluoro-4-(5-methylpyrazol-1-yl)phenyl]}-(2R,4R)-4-ethoxypyrrolidine-1,2-dicarboxamide,
1-[(4-ethynylphenyl)]-2-{[2-fluoro-4-(3-methylpyrazol-1-yl)phenyl]}-(2R,4R)-4-hydroxypyrrolidine-1,2-dicarboxamide,
1-[(4-ethynylphenyl)]-2-{[2-fluoro-4-(3-methylpyrazol-1-yl)phenyl]}-(2R,4R)-pyrrolidine-1,2-dicarboxamide,
1-[(4-ethynylphenyl)]-2-{[2-fluoro-4-(3-methylpyrazol-1-yl)phenyl]}-(2R,4R)-4-methoxypyrrolidine-1,2-dicarboxamide,
1-[(4-ethynylphenyl)]-2-{[2-fluoro-4-(3-methylpyrazol-1-yl)phenyl]}-(2R,4R)-4-ethoxypyrrolidine-1,2-dicarboxamide.

EXAMPLE 4

The following compounds are obtained analogously to Example 1:
1-[(4-ethynylphenyl)]-2-{[4-(2-oxopiperidin-1-yl)phenyl]}-(2R,4R)-4-ethoxypyrrolidine-1,2-dicarboxamide ("A4-1"),
1-[(4-ethynylphenyl)]-2-{[3-fluoro-4-(2-oxo-2H-pyridin-1-yl)phenyl]}-(2R,4R)-4-ethoxypyrrolidine-1,2-dicarboxamide ("A4-2"),
1-[(4-ethynylphenyl)]-2-{[4-(3-oxomorpholin-4-yl)phenyl]}-(2R,4R)-4-ethoxypyrrolidine-1,2-dicarboxamide,
1-[(4-ethynylphenyl)]-2-{[4-(3-oxomorpholin-4-yl)phenyl]}-(2S,4R)-4-ethoxypyrrolidine-1,2-dicarboxamide,
1-[(4-ethynylphenyl)]-2-{[4-(2-oxo-2H-pyrazin-1-yl)phenyl]}-(2R,4R)-4-ethoxypyrrolidine-1,2-dicarboxamide,
1-[(4-ethynylphenyl)]-2-{[4-(2-oxo-2H-pyrazin-1-yl)phenyl]}-(2S,4R)-4-ethoxypyrrolidine-1,2-dicarboxamide,
1-[(4-ethynylphenyl)]-2-{[4-(2-oxopiperidin-1-yl)phenyl]}-(2R,4R)-4-hydroxypyrrolidine-1,2-dicarboxamide,
1-[(4-ethynylphenyl)]-2-{[4-(2-oxopyrrolidin-1-yl)phenyl]}-(2R,4R)-4-hydroxypyrrolidine-1,2-dicarboxamide,
1-[(4-ethynylphenyl)]-2-{[3-methyl-4-(2-oxopiperidin-1-yl)phenyl]}-(2R,4R)-4-hydroxypyrrolidine-1,2-dicarboxamide,
1-[(4-ethynylphenyl)]-2-{[3-methyl-4-(2-oxopyrrolidin-1-yl)phenyl]}-(2R,4R)-4-hydroxypyrrolidine-1,2-dicarboxamide,
1-[(4-ethynylphenyl)]-2-{[3-fluoro-4-(3-oxomorpholin-4-yl)phenyl]}-(2R,4R)-4-ethoxypyrrolidine-1,2-dicarboxamide,
1-[(4-ethynylphenyl)]-2-{[3-fluoro-4-(3-oxomorpholin-4-yl)phenyl]}-(2S,4R)-4-ethoxypyrrolidine-1,2-dicarboxamide,
1-[(4-ethynyl phenyl)]-2-{[1-acetyl-2,3-dihydro-1H-indol-5-yl]}-(2R,4R)-4-hydroxypyrrolidine-1,2-dicarboxamide ("A4-3"),
1-[(4-ethynylphenyl))]-2-{[2-ethoxycarbonyl-1H-indol-5-yl]}-(2R,4R)-4-hydroxypyrrolidine-1,2-dicarboxamide,
1-[(4-ethynylphenyl)]-2-{[2-fluoro-4-(3-oxomorpholin-4-yl)phenyl]}-(2R,4R)-4-hydroxypyrrolidine-1,2-dicarboxamide,
1-[(4-ethynylphenyl)]-2-{[3-methoxy-4-(2-oxo-2H-pyridin-1-yl)phenyl]}-(2R,4R)-4-methoxypyrrolidine-1,2-dicarboxamide ("A4-4"),
1-[(4-ethynylphenyl)]-2-{[3-methyl-4-(3-oxomorpholin-4-yl)phenyl]}-(2R,4R)-4-hydroxypyrrolidine-1,2-dicarboxamide,
1-[(4-ethynylphenyl)]-2-{[4-(2-oxo-2H-pyridin-1-yl)phenyl]}-(2R,4R)-4-hydroxypyrrolidine-1,2-dicarboxamide,
1-[(4-ethynylphenyl)]-2-{[4-(3-oxomorpholin-4-yl)phenyl]}-(2R,4R)-4-allyloxypyrrolidine-1,2-dicarboxamide ("A4-5"),
1-[(4-ethynylphenyl)]-2-{[2-fluoro-4-(3-oxomorpholin-4-yl)phenyl]}-(2R,4R)-4-allyloxypyrrolidine-1,2-dicarboxamide,
1-[(4-ethynylphenyl)]-2-{[4-(3-oxomorpholin-4-yl)phenyl]}-(2R,4R)-4-propargyloxypyrrolidine-1,2-dicarboxamide ("A4-6"),
1-[(4-ethynylphenyl)]-2-{[2-fluoro-4-(3-oxomorpholin-4-yl)phenyl]}-(2R,4R)-4-propargyloxypyrrolidine-1,2-dicarboxamide,
1-[(4-ethynylphenyl))]-2-{[2-fluoro-4-(2-oxo-2H-pyridin-1-yl)phenyl]}-(2R,4R)-4-methoxypyrrolidine-1,2-dicarboxamide,
1-[(4-ethynylphenyl)]-2-{[4-(3-methyl-2-oxo-2H-pyridin-1-yl)phenyl]}-(2R,4R)-4-methoxypyrrolidine-1,2-dicarboxamide,
1-[(4-ethynylphenyl)]-2-{[2-fluoro-4-(3-oxomorpholin-4-yl)phenyl]}-(2R,4S)-4-propargyloxypyrrolidine-1,2-dicarboxamide,
1-[(4-ethynylphenyl)]-2-{[4-(3-oxomorpholin-4-yl)phenyl]}-(2R,4R)-4-(2,3-dihydroxypropoxy)pyrrolidine-1,2-dicarboxamide ("A4-7"),
1-[(4-ethynylphenyl)]-2-{[4-(5-methyl-2-oxo-2H-pyridin-1-yl)phenyl]}-(2R,4R)-4-methoxypyrrolidine-1,2-dicarboxamide,
1-[(4-ethynylphenyl))]-2-{[4-(2-methoxycarbonyl-4-hydroxypyrrolidin-1-yl)phenyl]}-(2R,4R)-4-methoxypyrrolidine-1,2-dicarboxamide ("A4-8"), m.p. 103°, 1-[(4-ethynylphenyl)]-2-{[2-fluoro-4-(3-methyl-2-oxo-2H-pyridin-1-yl)phenyl]}-(2S,4R)-4-methoxypyrrolidine-1,2-dicarboxamide, 1-[(4-ethynylphenyl)]-2-{[2-fluoro-4-(3-methyl-2-oxo-2H-pyridin-1-yl)phenyl]}-(2R,4R)-4-methoxypyrrolidine-1,2-dicarboxamide, 1-[(4-ethynylphenyl)]-2-{[4-(3-oxomorpholin-4-yl)-4-phenyl]}-(2R,4R)-4-(methoxyethoxy)pyrrolidine-1,2-dicarboxamide ("A4-9"), 1-[(4-ethynylphenyl)]-2-{[4-(3-oxomorpholin-4-yl)-phenyl]}-(2R,4R)-4-(methoxycarbonylmethoxy)pyrrolidine-1,2-dicarboxamide ("A4-10"), 1-[(4-ethynylphenyl)]-2-{[4-(3-oxomorpholin-4-yl)-phenyl]}-(2R,4R)-4-(carboxymethoxy)pyrrolidine-1,2-dicarboxamide ("A4-11"), 1-[(4-ethynylphenyl)]-2-{[4-(6-methyl-3-oxo-2H-pyridazin-2-yl)phenyl]}-(2R,4R)-4-methoxypyrrolidine-1,2-dicarboxamide ("A4-12"), 1-[(4-ethynylphenyl)]-2-{[2-methyl-4-(3-oxomorpholin-4-yl)phenyl]}-(2R,4R)-4-(methoxyethoxy)pyrrolidine-1,2-dicarboxamide, 1-[(4-ethynylphenyl)]-2-{[2-fluoro-4-(3-oxomorpholin-4-yl)phenyl]}-(2R,4R)-4-(methoxyethoxy)pyrrolidine-1,2-dicarboxamide.

Pharmacological data (affinity to receptors)

| Compound No. | FXa-IC$_{50}$ [M] | TF/FVIIa-IC$_{50}$ [M] |
| --- | --- | --- |
| "A1" | $1.3 \times 10^{-9}$ | $1.9 \times 10^{-9}$ |
| "A2" | $3.1 \times 10^{-9}$ | $3.2 \times 10^{-9}$ |
| "A4-1" | $3.0 \times 10^{-9}$ | |
| "A4-2" | $1.9 \times 10^{-9}$ | |
| "A4-3" | $2.6 \times 10^{-6}$ | |
| "A4-4" | $2.8 \times 10^{-9}$ | |
| "A4-5" | $3.1 \times 10^{-9}$ | |
| "A4-6" | $1.3 \times 10^{-9}$ | |
| "A4-7" | $3.1 \times 10^{-9}$ | |
| "A4-8" | $1.1 \times 10^{-6}$ | |
| "A4-9" | $3.3 \times 10^{-9}$ | |
| "A4-10" | $4.2 \times 10^{-9}$ | |
| "A4-11" | $4.8 \times 10^{-9}$ | |
| "A4-12" | $2.1 \times 10^{-6}$ | |

The following examples relate to medicaments:

EXAMPLE A

Injection Vials

A solution of 100 g of an active ingredient of the formula I and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions.

Each injection vial contains 5 mg of active ingredient.

EXAMPLE B

Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

EXAMPLE C

Solution

A solution is prepared from 1 g of an active ingredient of the formula I, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilized by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

EXAMPLE F

Coated Tablets

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced into hard gelatine capsules in a conventional manner in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:
1. Compounds of the formula I

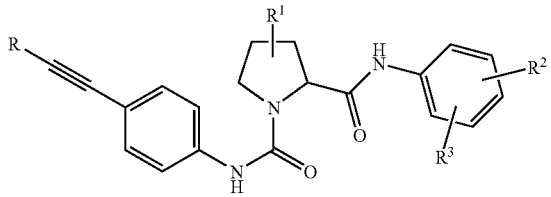

in which
R is H, X, A, X—CO— or A-CO—,
R¹ is H, =O, Hal, X, A, OH, OA, A-COO—, A-CONH—, A-CONA-, N₃, NH₂, NO₂, CN, COOH, COOA, CONH₂, CON(A)₂, O-allyl, O-propargyl, O-benzyl, =N—OH, =N—OA, OCH₂CH(OH)CH₂OH, A-O—CO—(CH₂)$_m$—O—, —O(CH₂)$_m$COOH or —O(CH₂)$_m$OA,
R² is H, Hal or A,
R³ is 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2-iminopiperidin-1-yl, 2-iminopyrrolidin-1-yl, 3-iminomorpholin-4-yl, 2-iminoimidazolidin-1-yl, 2-imino-1H-pyrazin-1-yl, 2,6-dioxopiperidin-1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl (=2-oxoazepan-1-yl), 2-azabicyclo[2.2.2]octan-3-on-2-yl, 5,6-dihydro-1H-pyrimidin-2-oxo-1-yl, 2-oxo-1,3-oxazinan-3-yl or 4H-1,4-oxazin-4-yl,
furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl or pyrazinyl,
optionally mono- or disubstituted by Hal, OA, OH, COOA and/or A, or
CONR⁴R⁵,
R² and R³ together are alternatively —CH=CH—NH— or —CH₂—CH₂—NH, where one H atom may be replaced by A-CO— or A-O—CO—,
R⁴ and R⁵, independently of one another, are H or A, or
R⁴ and R⁵ together are alternatively an alkylene chain having 3, 4 or 5 carbon atoms, which may also be substituted by A, Hal, OA and/or carbonyl oxygen (=CO),
X is aryl, arylalkyl, Het or Het-alkyl,
aryl is phenyl, naphthyl or biphenyl, each of which is unsubstituted or mono-, di- or trisubstituted by Hal, A, OH, NH₂, NO₂, CN, COOH, COOA, CONH₂, NHCOA, NHCONH₂, NHSO₂A, CHO, COA, SO₂NH₂, SO₂A, —CH₂—COOH or —OCH₂—COOH,
Het is a mono- or bicyclic saturated, unsaturated or aromatic heterocyclic radical having from 1 to 4 N, O and/or S atoms, which may be unsubstituted or mono-, di- or trisubstituted by Hal, A, benzyl, cycloalkyl, OH, NH₂, NHCONH₂, NO₂, CN, —CH₂—COOH, —CH₂—CONH₂, NHCOA, NR³SO₂A, CHO, SO₂NH₂, SO₂A and/or carbonyl oxygen,
A is unbranched, branched or cyclic alkyl having 1-10 carbon atoms, in which, in addition, 1-7 H atoms may be replaced by F and/or chlorine,
Hal is F, Cl, Br or I,
m is 1, 2, 3, 4, 5 or 6,
n is 0, 1, 2, 3, 4, 5 or 6,
or pharmaceutically acceptable salts, stereoisomers or mixtures thereof in all ratios.

2. Compounds according to claim 1, in which
R is H or A,
or pharmaceutically acceptable salts, stereoisomers or mixtures thereof in all ratios.

3. Compounds according to claim 1, in which
R is H, X, A, X—CO— or A-CO—,
R¹ is H, =O, Hal, X, A, OH, OA, A-COO—, A-CONH—, A-CONA-, N₃, NH₂, NO₂, CN, COOH, COOA, CONH₂, CON(A)₂, O-allyl, O-propargyl, O-benzyl, =N—OH, =N—OA, OCH₂CH(OH)CH₂OH, A-O—CO—(CH₂)$_m$—O—, —O(CH₂)$_m$COOH or —O(CH₂)$_m$OA,
R² is H, Hal or A,
R³ is 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2-iminopiperidin-1-yl, 2-iminopyrrolidin-1-yl, 3-iminomorpholin-4-yl, 2-iminoimidazolidin-1-yl, 2-imino-1H-pyrazin-1-yl, 2,6-dioxopiperidin-1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl (=2-oxoazepan-1-yl), 2-azabicyclo[2.2.2]octan-3-on-2-yl, 5,6-dihydro-1H-pyrimidin-2-oxo-1-yl, 2-oxo-1,3-oxazinan-3-yl or 4H-1,4-oxazin-4-yl,
furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl or pyrazinyl,
optionally mono- or disubstituted by Hal, OA, OH, COOA and/or A,
or
CONR⁴R⁵,
R⁴ and R⁵, independently of one another, are H or A, or
R⁴ and R⁵ together are alternatively an alkylene chain having 3, 4 or 5 carbon atoms,
X is aryl, arylalkyl, Het or Het-alkyl,
aryl is phenyl, naphthyl or biphenyl, each of which is unsubstituted or mono-, di- or trisubstituted by Hal, A, OH, NH₂, NO₂, CN, COOH, COOA, CONH₂, NHCOA, NHCONH₂, NHSO₂A, CHO, COA, SO₂NH₂, SO₂A, —CH₂—COOH or —OCH₂—COOH,
Het is a mono- or bicyclic saturated, unsaturated or aromatic heterocyclic radical having from 1 to 4 N, O and/or S atoms, which may be unsubstituted or mono-, di- or trisubstituted by Hal, A, benzyl, cycloalkyl, OH, NH₂, NHCONH₂, NO₂, CN, —CH₂—COOH, —CH₂—CONH₂, NHCOA, NR³SO₂A, CHO, SO₂NH₂, SO₂A and/or carbonyl oxygen,
A is unbranched, branched or cyclic alkyl having 1-10 carbon atoms, in which, in addition, 1-7 H atoms may be replaced by F,
Hal is F, Br or I,
or pharmaceutically acceptable salts, stereoisomers or mixtures thereof in all ratios.

4. Compounds according to claim 1, in which
R is H or A,
R¹ is H, OH, OA, O-allyl, O-propargyl, OCH₂CH(OH)CH₂OH, A-O—CO—(CH₂)$_m$—O—, —O(CH₂)$_m$COOH or —O(CH₂)$_m$OA,
R² is H, Hal or A,
R³ is 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2-oxopiperazin-1-yl, 3-oxo-2H-pyridazin-2-yl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl or pyrazinyl, optionally mono- or disubstituted by Hal, OA, OH, COOA and/or A, or $CONR^4R^5$, $R^4$ and $R^5$ together are an alkylene chain having 3, 4 or 5 carbon atoms, A is unbranched, branched or cyclic alkyl having 1-10 carbon atoms, in which, in addition, 1-7 H atoms may be replaced by F, Hal is F, Br or I, or pharmaceutically acceptable salts, stereoisomers or mixtures thereof in all ratios.

5. Compounds according to claim 1 in which

R is H, X, A, X—CO— or A-CO—, $R^1$ is H, =O, Hal, X, A, OH, OA, A-COO—, A-CONH—, A-CONA-, $N_3$, $NH_2$, $NO_2$, CN, COOH, COOA, $CONH_2$, $CON(A)_2$, O-allyl, O-propargyl, O-benzyl, =N—OH, =N—OA, $OCH_2CH(OH)CH_2OH$, A-O—CO—$(CH_2)_m$—O—, —$(CH_2)_m$COOH or —$O(CH_2)_m$OA, $R^2$ is H, Hal or A, $R^3$ is 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2-iminopiperidin-1-yl, 2-iminopyrrolidin-1-yl, 3-iminomorpholin-4-yl, 2-iminoimidazolidin-1-yl, 2-imino-1H-pyrazin-1-yl, 2,6-dioxopiperidin-1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl (=2-oxoazepan-1-yl), 2-azabicyclo[2.2.2]octan-3-on-2-yl, 5,6-dihydro-1H-pyrimidin-2-oxo-1-yl, 2-oxo-1,3-oxazinan-3-yl or 4H-1,4-oxazin-4-yl, X is aryl, arylalkyl, Het or Het-alkyl, aryl is phenyl, naphthyl or biphenyl, each of which is unsubstituted or mono-, di- or trisubstituted by Hal, A, OH, $NH_2$, $NO_2$, CN, COOH, COOA, $CONH_2$, NHCOA, $NHCONH_2$, $NHSO_2A$, CHO, COA, $SO_2NH_2$, $SO_2A$, —$CH_2$—COOH or —$OCH_2$—COOH, Het is a mono- or bicyclic saturated, unsaturated or aromatic heterocyclic radical having from 1 to 4 N, O and/or S atoms, which may be unsubstituted or mono-, di- or trisubstituted by Hal, A, benzyl, cycloalkyl, OH, $NH_2$, $NHCONH_2$, $NO_2$, CN, —$CH_2$—COOH, —$CH_2$-$CONH_2$, NHCOA, $NR^3SO_2A$, CHO, $SO_2NH_2$, $SO_2A$ and/or carbonyl oxygen, A is unbranched, branched or cyclic alkyl having 1-10 carbon atoms, in which, in addition, 1-7 H atoms may be replaced by F, Hal is F, Br or I, or pharmaceutically acceptable salts, stereoisomers or mixtures thereof in all ratios.

6. Compounds according to claim 1, in which $R^3$ is 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2-oxopiperazin-1-yl or 3-oxo-2H-pyridazin-2-yl, or pharmaceutically acceptable salts, stereoisomers or mixtures thereof in all ratios.

7. Compounds according to claim 1, in which $R^1$ is H, OH, OA, O-allyl, O-propargyl, $OCH_2CH(OH)CH_2OH$, A-O—CO—$(CH_2)_m$—O—, —$O(CH_2)_m$COOH or —$O(CH_2)_m$OA, or pharmaceutically acceptable salts, stereoisomers or mixtures thereof in all ratios.

8. Compounds according to claim 1, in which

A is unbranched or branched alkyl having 1-6 carbon atoms, or pharmaceutically acceptable salts, stereoisomers or mixtures thereof in all ratios.

9. Compounds according to claim 1, in which

R is H or A, $R^1$ is H, OH, OA, O-allyl, O-propargyl, $OCH_2CH(OH)CH_2OH$, A-O—CO—$(CH_2)_m$—O—, —$O(CH_2)_m$COOH or —$O(CH_2)_m$OA, $R^2$ is H, Hal or A, $R^3$ is 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2-oxopiperazin-1-yl or 3-oxo-2H-pyridazin-2-yl, optionally monosubstituted by A, OH or COOA, A is unbranched, branched or cyclic alkyl having 1-10 carbon atoms, in which, in addition, 1-7 H atoms may be replaced by F, Hal is F, Cl, Br or I, or pharmaceutically acceptable salts, stereoisomers or mixtures thereof in all ratios.

10. Compounds according to claim 1 selected from the group consisting of

1-[(4-ethynylphenyl)]-2-{[4-(2-oxo-2H-pyridin-1-yl)phenyl]}-(2R,4R)-4-methoxypyrrolidine-1,2-dicarboxamide, 1-[(4-ethynylphenyl)]-2-{[4-(3-oxomorpholin-4-yl)phenyl]}-(2R,4R)-4-methoxypyrrolidine-1,2-dicarboxamide, 1-[(4-ethynylphenyl)]-2-{[3-methyl-4-(3-oxomorpholin-4-yl)phenyl]}-(2R,4R)-4-methoxypyffolidine-1,2-dicarboxamide, 1-[(4-ethynylphenyl)]-2-{[4-(3-oxomorpholin-4-yl)phenyl]}-(2R,4R)-4-hydroxypyrrolidine-1,2-dicarboxamide, 1-[(4-ethynylphenyl)]-2-{[3-methyl-4-(3-oxomorpholin-4-yl)phenyl]}-(2R,4R)-4-ethoxypyrrolidine-1,2-dicarboxamide, 1-[(4-ethynylphenyl)]-2-{[4-(2-oxo-2H-pyridin-1-yl)phenyl]}-(2R,4R)-4-hydroxypyrrolidine-1,2-dicarboxamide, 1-[(4-ethynylphenyl)]-2-{[3-methyl-4-(3-oxomorpholin-4-yl)phenyl]}-(2R,4R)-4-hydroxypyrrolidine-1,2-dicarboxamide, 1-[(4-ethynylphenyl)]-2-{[4-(3-oxomorpholin-4-yl)phenyl]}-(2R)-pyrrolidine-1,2-dicarboxamide, 1-[(4-ethynylphenyl)]-2-{[3-methyl-4-(3-oxomorpholin-4-yl)phenyl]}-(2R)-pyrrolidine-1,2-dicarboxamide, 1-[(4-ethynylphenyl)]-2-{[4-(2-oxo-2H-pyridin-1-yl)phenyl]}-(2R)-pyrrolidine-1,2-dicarboxamide, 1-[(4-ethynylphenyl)]-2-{[2-fluoro-4-(3-oxomorpholin-4-yl)phenyl]}-(2R,4R)-4-methoxypyrrolidine-1,2-dicarboxamide, 1-[(4-ethynylphenyl)]-2-{[4-(2-oxo-2H-pyridin-1-yl)phenyl]}-(2R,4R)-4-ethoxypyrrolidine-1,2-dicarboxamide, 1-[(4-ethynylphenyl)]-2-{[3-methyl-4-(3-oxomorpholin-4-yl)phenyl]}-(2R,4R)-4-ethoxypyrrolidine-1,2-dicarboxamide, 1-[(4-ethynylphenyl)]-2-{[2-fluoro-4-(3-oxomorpholin-4-yl)phenyl]}-(2R)-pyrrolidine-1,2-dicarboxamide,
1-[(4-ethynylphenyl)]-2-{[2-fluoro-4-(3-oxomorpholin-4-yl)phenyl]}-(2R,4R)-4-ethoxypyrrolidine-1,2-dicarboxamide,
1-[(4-ethynylphenyl)]-2-{[2-fluoro-4-(3-oxomorpholin-4-yl)phenyl]}-(2R,4R)-4-hydroxypyrrolidine-1,2-dicarboxamide,
1-[(4-ethynylphenyl)]-2-{[4-(2-oxo-1H-pyrazin-1-yl)phenyl]}-(2R,4R)-4-ethoxypyrrolidine-1,2-dicarboxamide,
1-[(4-ethynylphenyl)]-2-{[4-(2-oxopiperidin-1-yl)phenyl]}-(2R,4R)-4-ethoxypyrrolidine-1,2-dicarboxamide,
1-[(4-ethynylphenyl)]-2-{[3-fluor-4-(2-oxo-2H-pyridin-1-yl)-phenyl]}-(2R,4R)-4-ethoxypyrrolidine-1,2-dicarboxamide,
1-[(4-ethynylphenyl)]-2-{[4-(3-oxomorpholin-4-yl)phenyl]}-(2R,4R)-4-ethoxypyrrolidine-1,2-dicarboxamide,
1-[(4-ethynylphenyl)]-2-{[4-(3-oxomorpholin-4-yl)phenyl]}-(2S,4R)-4-ethoxypyrrolidine-1,2-dicarboxamide,
1-[(4-ethynylphenyl)]-2-{[4-(2-oxo-2H-pyrazin-1-yl)phenyl]}-(2R,4R)-4-ethoxypyrrolidine-1,2-dicarboxamide,
1-[(4-ethynylphenyl)]-2-{[4-(2-oxo-2H-pyrazin-1-yl)phenyl]}-(2S,4R)-4-ethoxypyrrolidine-1,2-dicarboxamide,
1-[(4-ethynylphenyl)]-2-{[4-(2-oxopiperidin-1-yl)phenyl]}-(2R,4R)-4-hydroxypyrrolidine-1,2-dicarboxamide,
1-[(4-ethynylphenyl)]-2-{[4-(2-oxopyrrolidin-1-yl)phenyl]}-(2R,4R)-4-hydroxypyrrolidine-1,2-dicarboxamide,
1-[(4-ethynylphenyl)]-2-{[3-methyl-4-(2-oxopiperidin-1-yl)phenyl]}-(2R,4R)-4-hydroxypyrrolidine-1,2-dicarboxamide,
1-[(4-ethynylphenyl)]-2-{[3-methyl-4-(2-oxopyrrolidin-1-yl)phenyl]}-(2R,4R)-4-hydroxypyrrolidine-1,2-dicarboxamide,
1-[(4-ethynylphenyl)]-2-{[3-fluoro-4-(3-oxomorpholin-4-yl)phenyl]}-(2R,4R)-4-ethoxypyrrolidine-1,2-dicarboxamide,
1-[(4-ethynylphenyl)]-2-{[3-fluoro-4-(3-oxomorpholin-4-yl)phenyl]}-(2S,4R)-4-ethoxypyrrolidine-1,2-dicarboxamide,
1-[(4-ethynylphenyl)]-2-{[1-acetyl-2,3-dihydro-1H-indol-5-yl]}-(2R,4R)-4-hydroxypyrrolidine-1,2-dicarboxamide,
1-[(4-ethynylphenyl)]-2-{[2-ethoxycarbonyl-1H-indol-5-yl]}-(2R,4R)-4-hydroxypyrrolidine-1,2-dicarboxamide,
1-[(4-ethynylphenyl)]-2-{[2-fluoro-4-(3-oxomorpholin-4-yl)phenyl]}-(2R,4R)-4-hydroxypyrrolidine-1,2-dicarboxamide,
1-[(4-ethynylphenyl)]-2-{[3-methoxy-4-(2-oxo-2H-pyridin-1-yl)phenyl]}-(2R,4R)-4-methoxypyrrolidine-1,2-dicarboxamide,
1-[(4-ethynylphenyl)]-2-{[3-methyl-4-(3-oxomorpholin-4-yl)phenyl]}-(2R,4R)-4-hydroxypyrrolidine-1,2-dicarboxamide,
1-[(4-ethynylphenyl)]-2-{[4-(2-oxo-2H-pyridin-1-yl)phenyl]}-(2R,4R)-4-hydroxypyrrolidine-1,2-dicarboxamide,
1-[(4-ethynylphenyl)]-2-{[4-(3-oxomorpholin-4-yl)phenyl]}-(2R,4R)-4-allyloxypyrrolidine-1,2-dicarboxamide,
1-[(4-ethynylphenyl)]-2-{[2-fluoro-4-(3-oxomorpholin-4-yl)phenyl]}-(2R,4R)-4-allyloxypyrrolidine-1,2-dicarboxamide,
1-[(4-ethynylphenyl)]-2-{[4-(3-oxomorpholin-4-yl)phenyl]}-(2R,4R)-4-propargyloxypyrrolidine-1,2-dicarboxamide,
1-[(4-ethynylphenyl)]-2-{[2-fluoro-4-(3-oxomorpholin-4-yl)phenyl]}-(2R,4R)-4-propargyloxypyrrolidine-1,2-dicarboxamide,
1-[(4-ethynylphenyl)]-2-{[2-fluoro-4-(2-oxo-2H-pyridin-1-yl)phenyl]}-(2R,4R)-4-methoxypyrrolidine-1,2-dicarboxamide,
1-[(4-ethynylphenyl)]-2-{[4-(3-methyl-2-oxo-2H-pyridin-1-yl)phenyl]}-(2R,4R)-4-methoxypyrrolidine-1,2-dicarboxamide,
1-[(4-ethynylphenyl)]-2-{[2-fluoro-4-(3-oxomorpholin-4-yl)phenyl]}-(2R,4S)-4-propargyloxypyrrolidine-1,2-dicarboxamide,
1-[(4-ethynylphenyl)]-2-{[4-(3-oxomorpholin-4-yl)phenyl]}-(2R,4R)-4-(2,3-dihydroxypropoxy)pyrrolidine-1,2-dicarboxamide,
1-[(4-ethynylphenyl)]-2-{[4-(5-methyl-2-oxo-2H-pyridin-1-yl)phenyl]}-(2R,4R)-4-methoxypyrrolidine-1,2-dicarboxamide,
1-[(4-ethynylphenyl)]-2-{[4-(2-methoxycarbonyl-4-hydroxypyrrolidin-1-yl)phenyl]}-(2R,4R) -4-methoxypyrrolidine-1,2-dicarboxamide,
1-[(4-ethynylphenyl)]-2-{[2-fluoro-4-(3-methyl-2-oxo-2H-pyridin-1-yl)phenyl]}-(2S,4R)-4-methoxypyrrolidine-1,2-dicarboxamide,
1-[(4-ethynylphenyl)]-2-{[2-fluoro-4-(3-methyl-2-oxo-2H-pyridin-1-yl)phenyl]}-(2R,4R)-4-methoxypyrrolidine-1,2-dicarboxamide,
1-[(4-ethynylphenyl)]-2-{[4-(3-oxomorpholin-4-yl)phenyl]}-(2R,4R)-4-(methoxyethoxy)pyrrolidine-1,2-dicarboxamide,
1-[(4-ethynylphenyl)]-2-{[4-(3-oxomorpholin-4-yl)phenyl]}-(2R,4R)-4-(methoxycarbonylmethoxy)pyrrolidine-1,2-dicarboxamide,
1-[(4-ethynylphenyl)]-2-{[4-(3-oxomorpholin-4-yl)phenyl]}-(2R,4R)-4-(carboxymethoxy)pyrrolidine-1,2-dicarboxamide,
1-[(4-ethynylphenyl)]-2-{[4-(6-methyl-3-oxo-2H-pyridazin-2-yl)phenyl]}-(2R,4R)-4-methoxypyrrolidine-1,2-dicarboxamide,
1-[(4-ethynylphenyl)]-2-{[2-methyl-4-(3-oxomorpholin-4-yl)phenyl]}-(2R,4R)-4-(methoxyethoxy)pyrrolidine-1,2-dicarboxamide, and
1-[(4-ethynylphenyl)]-2-{[2-fluoro-4-(3-oxomorpholin-4-yl)phenyl]}-(2R,4R)-4-(methoxyethoxy)pyrrolidine-1,2-dicarboxamide, or pharmaceutically acceptable salts, or stereoisomers or mixtures thereof in all ratios.

11. Process for the preparation of compounds of the formula I according to claim 1 or pharmaceutically acceptable salts or stereoisomers thereof, comprising reacting a) a compound of the formula II

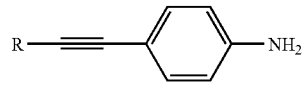

II in which R is as defined in claim 1, is reacted with a chloroformate compound to give a carbamate compound intermediate,
and subsequently reacting said intermediate with a compound of the formula III

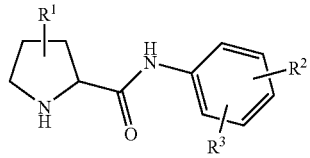

III in which
$R^1$, $R^2$ and $R^3$ as defined in claim 1,
or
b) reacting a compound of the formula III with a compound of the formula IV

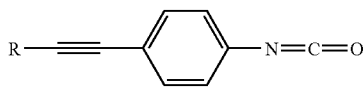

IV in which
R is as defined in claim 1,
or
c) reacting a compound of the formula V

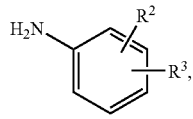

V in which $R^2$ and $R^3$ as defined in claim 1,
with a compound of the formula VI

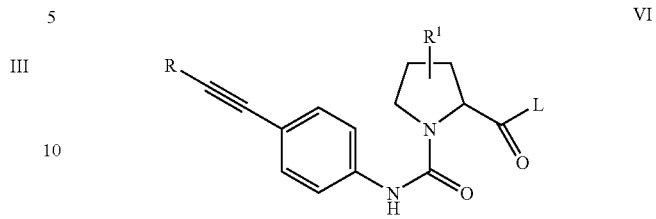

VI in which
L is Cl, Br, I or a free or reactively functionally modified OH group, and
R and $R^1$ are as defined in claim 1,
and/or converting a base or acid of the formula I is converted into one of its salts.

12. Medicaments comprising at least one compound of the formula I according to claim 1, and/or pharmaceutically acceptable, salts, stereoisomers or mixtures thereof in all ratios, and, optionally, excipients and/or adjuvants.

13. A method for the treatment of thromboses, myocardial infarction, arteriosclerosis, apoplexia, angina pectoris, restenosis after angioplasty, or claudicatio intermittens, comprising administering a compound according to claim 1, or a salt thereof, or stereoisomer or mixture thereof to a host in need thereof.

14. A pharmaceutical composition comprising a compound according to claim 1, a salt, stereoisomer or mixture thereof, and a pharmaceutically acceptable carrier.

15. A method according to claim 13, wherein the compound is administered with tissue plasminogen activator, streptokinase, urokinase, asprin or blood platelet glycoprotein receptor IIb/IIIb antagonists.

* * * * *

UNITED STATES PATENT AND TRADEMARK OFFICE
CERTIFICATE OF CORRECTION

PATENT NO. : 7,557,222 B2  Page 1 of 1
APPLICATION NO. : 10/561227
DATED : July 7, 2009
INVENTOR(S) : Mederski et al.

It is certified that error appears in the above-identified patent and that said Letters Patent is hereby corrected as shown below:

Column 22, line 57 reads:
"Hal is F, Br or I," should read: --Hal is F, Cl, Br or I,--

Column 24, lines 30 and 31 read:
"10. Compounds according to claim 1 selected from the group consisting of"
should read: --10. Compounds according to claim 1--

Column 26, line 49 reads: "1,2-dicarboxamide, and" should read: --1,2-dicarboxamide,--

Signed and Sealed this

Eighteenth Day of May, 2010

David J. Kappos
*Director of the United States Patent and Trademark Office*